United States Patent
Michelson

(10) Patent No.: US 8,048,076 B2
(45) Date of Patent: Nov. 1, 2011

(54) METHOD FOR INSTALLATION OF ANTERIOR CERVICAL PLATE SYSTEM HAVING VERTEBRAL BODY ENGAGING ANCHORS AND CONNECTING PLATE

(75) Inventor: Gary K. Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1729 days.

(21) Appl. No.: 11/114,540

(22) Filed: Apr. 26, 2005

(65) Prior Publication Data
US 2005/0187554 A1    Aug. 25, 2005

Related U.S. Application Data

(62) Division of application No. 10/160,408, filed on Jun. 4, 2002, now Pat. No. 7,740,630.

(60) Provisional application No. 60/296,061, filed on Jun. 4, 2001.

(51) Int. Cl.
*A61B 17/58* (2006.01)

(52) U.S. Cl. .................................................. 606/71

(58) Field of Classification Search .......... 606/60, 606/246, 279, 280, 70, 71, 281–299
See application file for complete search history.

(56) References Cited

U.S. PATENT DOCUMENTS

| | | |
|---|---|---|
| 1,105,105 A | 7/1914 | Sherman |
| 3,604,414 A | 9/1971 | Borges |
| 3,659,595 A | 5/1972 | Haboush |
| 3,900,025 A | 8/1975 | Barnes, Jr. |
| 3,960,147 A | 6/1976 | Murray |
| 4,034,418 A | 7/1977 | Jackson |
| 4,289,123 A | 9/1981 | Dunn |
| RE31,628 E | 7/1984 | Allgower et al. |
| 4,488,543 A | 12/1984 | Tornier |
| 4,493,317 A | 1/1985 | Klaue |
| 4,503,848 A | 3/1985 | Caspar et al. |
| 4,599,086 A | 7/1986 | Doty |
| 4,651,724 A | 3/1987 | Berentey et al. |
| 4,794,918 A | 1/1989 | Wolter |
| 4,936,848 A | 6/1990 | Bagby |
| 5,041,113 A | 8/1991 | Biedermann et al. |
| 5,053,036 A | 10/1991 | Perren et al. |
| 5,127,912 A | 7/1992 | Ray et al. |

(Continued)

FOREIGN PATENT DOCUMENTS

DE    4007306    5/1991

(Continued)

OTHER PUBLICATIONS

Advertisement for Codman Anterior Cervical Plate System by Codman; Johnson & Johnson; Professional, Inc.; undated.

(Continued)

*Primary Examiner* — Thomas Barrett
*Assistant Examiner* — Michael Araj
(74) *Attorney, Agent, or Firm* — Martin & Ferraro, LLP

(57) ABSTRACT

An anterior cervical plating system includes vertebral body engaging anchors coupled to a connecting plate in moveable relationship to vary the spacing between the anchoring points of the plating system to the vertebral bodies and to allow and/or cause intersegmental compression of vertebral bodies. The plating system includes instrumentation and method for installation thereof. The plating system is capable of both passive and active dynamization and the ability to produce the former from the latter.

36 Claims, 7 Drawing Sheets

U.S. PATENT DOCUMENTS

| | | | |
|---|---|---|---|
| 5,129,903 | A | 7/1992 | Luhr et al. |
| 5,147,361 | A | 9/1992 | Ojima et al. |
| 5,180,381 | A | 1/1993 | Aust et al. |
| 5,190,544 | A | 3/1993 | Chapman et al. |
| 5,209,751 | A | 5/1993 | Farris et al. |
| 5,234,431 | A | 8/1993 | Keller |
| 5,300,073 | A | 4/1994 | Ray et al. |
| 5,330,477 | A | 7/1994 | Crook |
| 5,344,421 | A | 9/1994 | Crook |
| 5,364,399 | A | 11/1994 | Lowery et al. |
| 5,397,363 | A | 3/1995 | Gelbard |
| 5,423,826 | A | 6/1995 | Coates et al. |
| 5,470,333 | A | 11/1995 | Ray |
| 5,520,690 | A | 5/1996 | Errico et al. |
| 5,531,746 | A | 7/1996 | Errico et al. |
| 5,531,747 | A | 7/1996 | Ray |
| 5,549,612 | A | 8/1996 | Yapp et al. |
| 5,558,674 | A | 9/1996 | Heggeness et al. |
| 5,569,250 | A | 10/1996 | Sarver et al. |
| 5,578,034 | A | 11/1996 | Estes |
| 5,593,409 | A | 1/1997 | Michelson |
| 5,601,553 | A | 2/1997 | Trebing et al. |
| 5,605,938 | A | 2/1997 | Roufa et al. |
| 5,607,426 | A | 3/1997 | Ralph et al. |
| 5,616,142 | A | 4/1997 | Yuan et al. |
| 5,628,781 | A | 5/1997 | Williams et al. |
| 5,643,265 | A | 7/1997 | Errico et al. |
| 5,662,652 | A | 9/1997 | Schafer et al. |
| 5,672,177 | A | 9/1997 | Seldin |
| 5,676,666 | A | 10/1997 | Oxland et al. |
| 5,676,703 | A | 10/1997 | Gelbard |
| 5,681,313 | A | 10/1997 | Diez |
| 5,713,900 | A | 2/1998 | Benzel et al. |
| 5,722,977 | A | 3/1998 | Wilhelmy |
| 5,728,127 | A | 3/1998 | Asher et al. |
| 5,735,853 | A | 4/1998 | Olerud |
| 5,735,899 | A | 4/1998 | Schwartz et al. |
| 5,741,258 | A | 4/1998 | Klaue et al. |
| 5,755,796 | A | 5/1998 | Ibo et al. |
| 5,766,254 | A | 6/1998 | Gelbard |
| 5,800,433 | A | 9/1998 | Benzel et al. |
| D402,032 | S | 12/1998 | Stone |
| 5,843,082 | A | 12/1998 | Yuan et al. |
| 5,865,848 | A | 2/1999 | Baker |
| 5,866,113 | A | 2/1999 | Hendriks et al. |
| D406,646 | S | 3/1999 | Stone |
| 5,876,402 | A | 3/1999 | Errico |
| 5,899,939 | A | 5/1999 | Boyce et al. |
| 5,902,304 | A | 5/1999 | Walker et al. |
| 5,904,683 | A | 5/1999 | Pohndorf et al. |
| 5,947,893 | A | 9/1999 | Agrawal et al. |
| 5,951,558 | A | 9/1999 | Fiz |
| 5,954,722 | A | 9/1999 | Bono |
| 5,954,725 | A | 9/1999 | Sherman et al. |
| 5,964,760 | A | 10/1999 | Richelsoph |
| 5,964,762 | A | 10/1999 | Biedermann et al. |
| 5,964,763 | A | 10/1999 | Incavo et al. |
| 5,968,098 | A | 10/1999 | Winslow |
| 6,022,350 | A | 2/2000 | Ganem |
| 6,030,389 | A | 2/2000 | Wagner et al. |
| 6,106,527 | A | 8/2000 | Wu et al. |
| 6,106,557 | A | 8/2000 | Robioneck et al. |
| 6,117,135 | A | 9/2000 | Schlapfer |
| 6,136,001 | A | 10/2000 | Michelson |
| 6,139,316 | A | 10/2000 | Sachdeva et al. |
| 6,139,550 | A | 10/2000 | Michelson |
| 6,152,927 | A | 11/2000 | Farris et al. |
| 6,159,213 | A | 12/2000 | Rogozinski |
| 6,193,721 | B1 | 2/2001 | Michelson |
| D440,311 | S | 4/2001 | Michelson |
| 6,224,602 | B1 | 5/2001 | Hayes |
| 6,224,607 | B1 | 5/2001 | Michelson |
| 6,228,085 | B1 | 5/2001 | Theken et al. |
| 6,235,034 | B1 | 5/2001 | Bray |
| 6,235,059 | B1 | 5/2001 | Benezech et al. |
| 6,258,089 | B1 | 7/2001 | Campbell et al. |
| 6,277,124 | B1 | 8/2001 | Haag |
| D449,692 | S | 10/2001 | Michelson |
| 6,296,647 | B1 | 10/2001 | Robioneck et al. |
| 6,302,883 | B1 | 10/2001 | Bono |
| 6,306,136 | B1 | 10/2001 | Baccelli |
| 6,328,738 | B1 | 12/2001 | Suddaby |
| 6,342,055 | B1 | 1/2002 | Eisermann et al. |
| 6,355,036 | B1 | 3/2002 | Nakajima |
| 6,383,189 | B1 | 5/2002 | Schumacher |
| 6,395,030 | B1 * | 5/2002 | Songer et al. ............... 623/17.11 |
| 6,402,756 | B1 | 6/2002 | Ralph et al. |
| 6,406,478 | B1 | 6/2002 | Kuo |
| 6,413,259 | B1 | 7/2002 | Lyons et al. |
| 6,471,706 | B1 | 10/2002 | Schumacher et al. |
| 6,503,250 | B2 | 1/2003 | Paul |
| 6,558,686 | B1 | 5/2003 | Darouiche |
| 6,576,017 | B2 | 6/2003 | Foley et al. |
| 6,585,738 | B1 | 7/2003 | Mangione et al. |
| 6,645,208 | B2 | 11/2003 | Apfelbaum et al. |
| 6,652,525 | B1 | 11/2003 | Assaker et al. |
| 6,699,249 | B2 | 3/2004 | Schlapfer et al. |
| 6,702,817 | B2 | 3/2004 | Beger et al. |
| 6,764,489 | B2 | 7/2004 | Ferree |
| 6,783,526 | B1 | 8/2004 | Lin et al. |
| 6,786,910 | B2 | 9/2004 | Cohen et al. |
| 6,793,658 | B2 | 9/2004 | LeHuec et al. |
| 6,855,147 | B2 | 2/2005 | Harrington, Jr. |
| 6,872,210 | B2 | 3/2005 | Hearn |
| 6,908,469 | B2 | 6/2005 | Sellers et al. |
| 7,112,202 | B2 | 9/2006 | Michelson |
| 7,115,130 | B2 | 10/2006 | Michelson |
| 7,201,753 | B2 | 4/2007 | Schlapfer et al. |
| 7,399,301 | B2 | 7/2008 | Michelson |
| 7,547,306 | B2 | 6/2009 | Michelson |
| 7,621,943 | B2 | 11/2009 | Michelson |
| 7,704,250 | B2 | 4/2010 | Michelson |
| 7,740,630 | B2 | 6/2010 | Michelson |
| 2001/0049559 | A1 | 12/2001 | Koo et al. |
| 2002/0004660 | A1 | 1/2002 | Henniges et al. |
| 2002/0111630 | A1 | 8/2002 | Ralph et al. |
| 2002/0183755 | A1 | 12/2002 | Michelson |
| 2002/0183756 | A1 | 12/2002 | Michelson |
| 2002/0183757 | A1 | 12/2002 | Michelson |
| 2002/0188296 | A1 | 12/2002 | Michelson |
| 2003/0036759 | A1 | 2/2003 | Musso |
| 2003/0060828 | A1 | 3/2003 | Michelson |
| 2003/0229348 | A1 | 12/2003 | Sevrain |
| 2004/0167521 | A1 | 8/2004 | De Windt |
| 2005/0027297 | A1 | 2/2005 | Michelson |
| 2005/0027298 | A1 | 2/2005 | Michelson |
| 2005/0085816 | A1 | 4/2005 | Michelson |
| 2005/0187554 | A1 | 8/2005 | Michelson |
| 2005/0192576 | A1 | 9/2005 | Michelson |
| 2005/0216010 | A1 | 9/2005 | Michelson |
| 2006/0085001 | A1 | 4/2006 | Michelson |
| 2009/0259226 | A1 | 10/2009 | Michelson |

FOREIGN PATENT DOCUMENTS

| | | |
|---|---|---|
| DE | 4409833 | 10/1995 |
| DE | 4414781 | 11/1995 |
| DE | 44 38 264 A | 3/1996 |
| DE | 19542064 | 6/1997 |
| WO | WO 94/26193 | 11/1994 |
| WO | WO 95/35067 | 12/1995 |
| WO | WO 96/08206 | 3/1996 |
| WO | WO 96/39975 | 12/1996 |
| WO | WO 99/56653 | 11/1999 |
| WO | WO 01/26566 | 4/2001 |
| WO | WO 01/89428 | 11/2001 |
| WO | WO 02/085226 | 10/2002 |

OTHER PUBLICATIONS

Aesculap Scientific Information Booklet; *Anterior Cervical Fusion and Interbody Stabilization with the Trapezial Osteosynthetic Plate Technique* by Wolfhard Casper: Feb. 1986.

Synthes Brochure: Spine for *Cervical Spine Locking Plate*; 1991.

Orion Brochure: *Anterior Cervical Plate System, Surgical Technique*, as described by Gary L. Lowery, M.D., Ph.D.; 1996.

Codman Brochure: *Anterior Cervical Plate System*; Sep. 1995.

Spinal Concepts Brochure: *The AcuFix, Anterior Cervical Plate System*; Undated.

EBI Brochure: *Introducing EBI VueLock, Anterior Cervical Plate System*; 2001.

Blackstone Brochure: *Blackstone Anterior Cervical Plate*; Undated.

Alphatec Manufacturing Brochure: *Deltaloc, Anterior Cervical Plate System*; Undated.

Sofamor Danek Brochure: *Atlantis, Anterior Cervical Plate System*; Undated.

Ortho Development Brochure: *Ortho Development Cervical Plate*; Undated.

Osteotech Brochure: *Affirm, Anterior Cervical Plate System*; Undated.

* cited by examiner

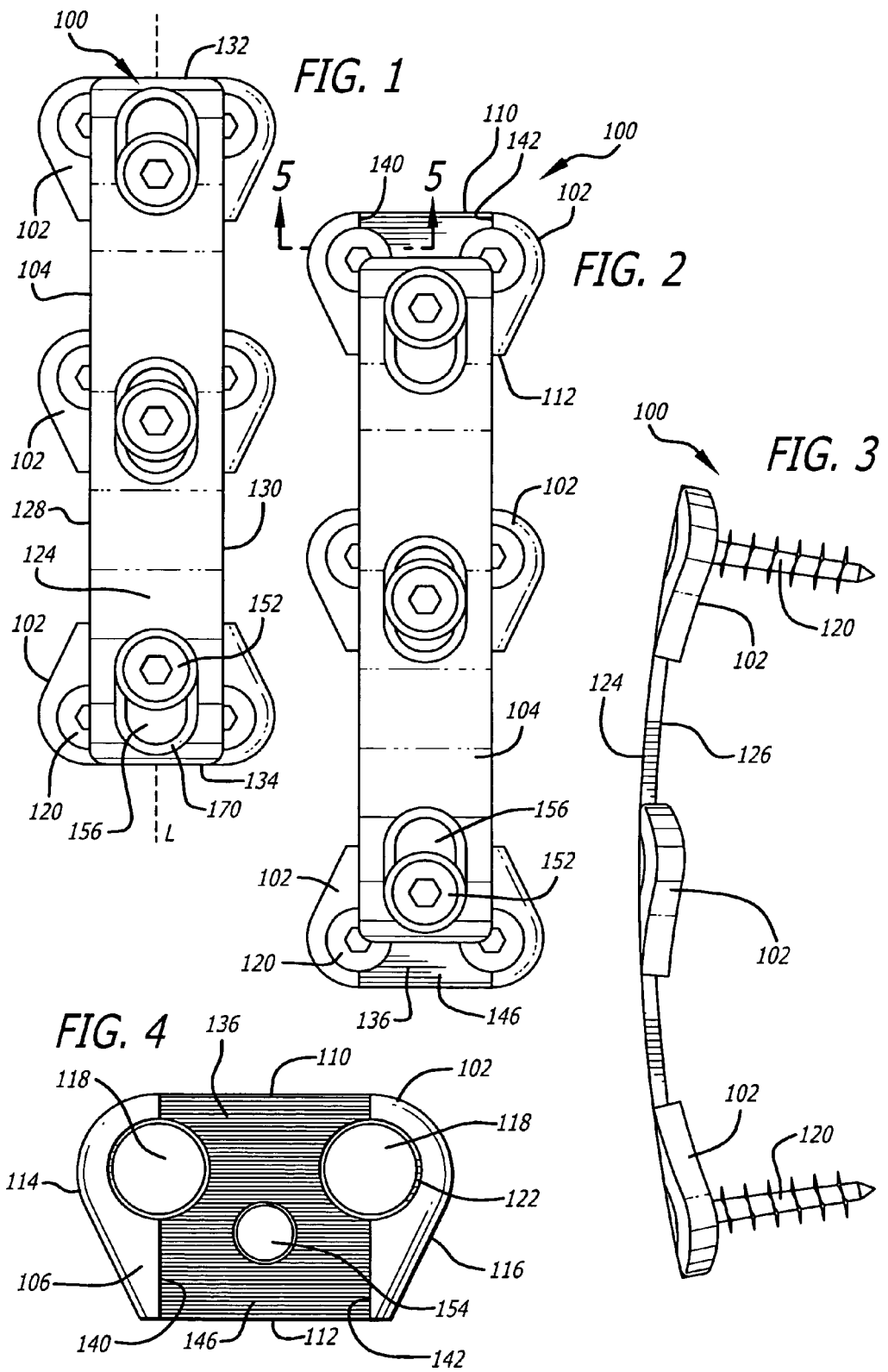

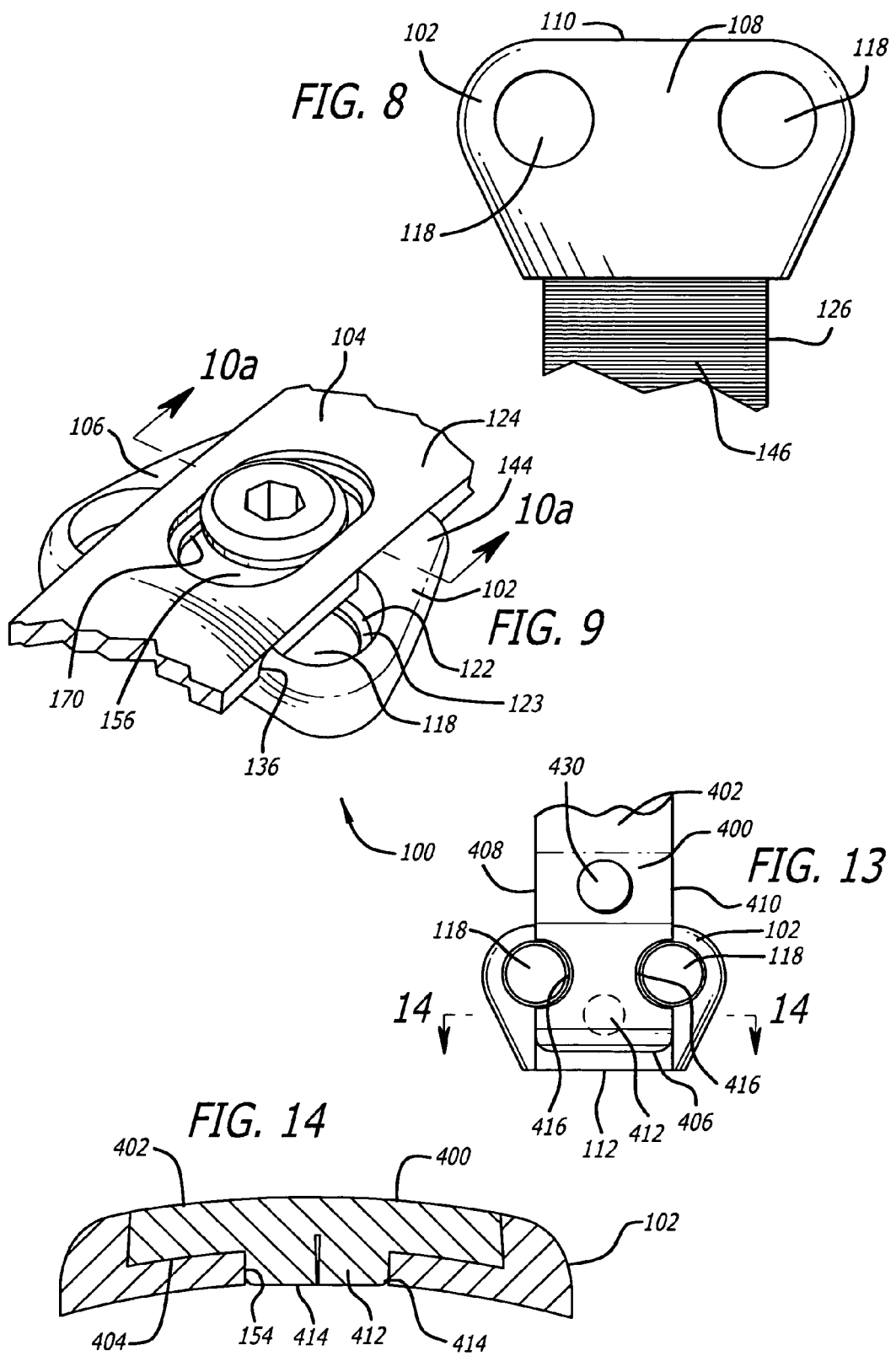

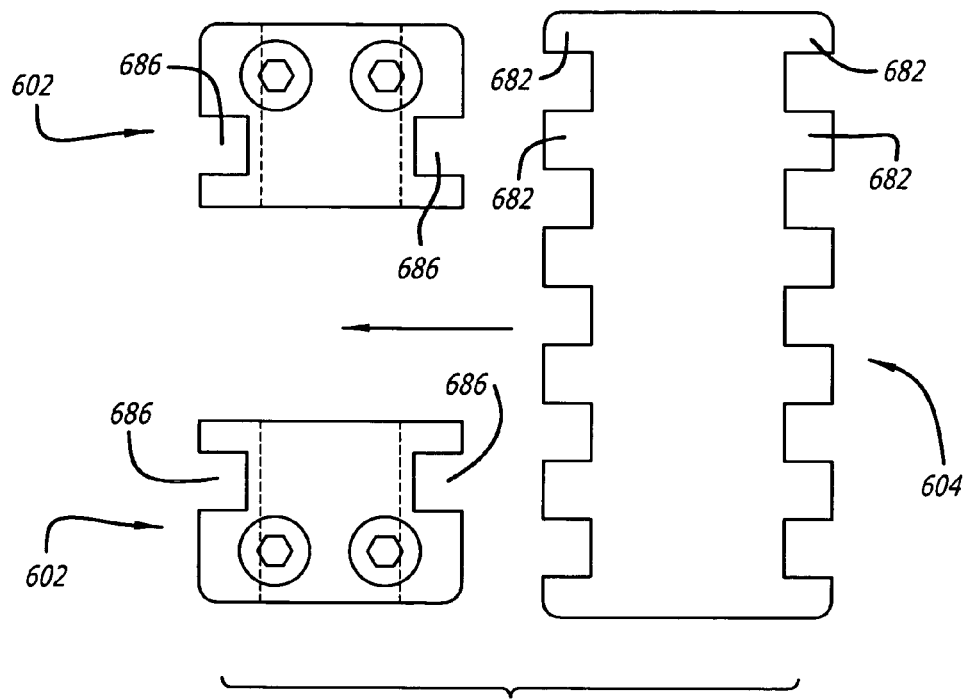
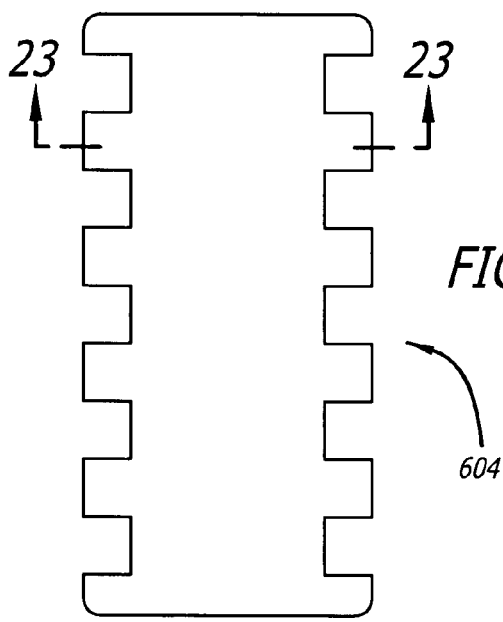
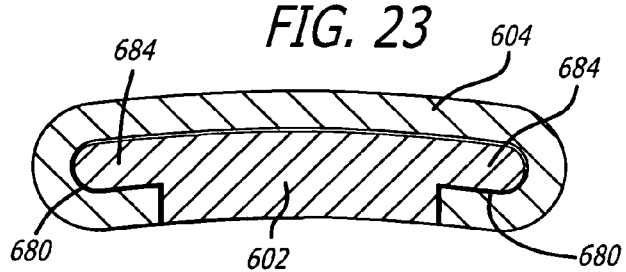
FIG. 21
FIG. 22
FIG. 23

METHOD FOR INSTALLATION OF ANTERIOR CERVICAL PLATE SYSTEM HAVING VERTEBRAL BODY ENGAGING ANCHORS AND CONNECTING PLATE

RELATED APPLICATIONS

This application is a divisional of application Ser. No. 10/160,408, filed Jun. 4, 2002, now U.S. Pat. No. 7,740,630, which claims the benefit of Provisional Application No. 60/296,061, filed Jun. 4, 2001; all of which are incorporated by reference herein.

BACKGROUND

The use of plates, screws, and locks to prevent separation and backing out of screws from the plate, for use on the anterior aspect of the cervical spine to provide alignment and stability as an adjunct to fusion of adjacent vertebral bodies, is known in the art.

The size of the vertebral bodies and the spacing between the vertebral bodies varies from patient to patient. The height of the vertebral bodies and the discs therebetween may vary level by level even in the same person. Thus, a plate of correct length does not necessarily have bone screw receiving holes correctly positioned to overlie the vertebral bodies in accordance with the spacing of the vertebral bodies to which the plate is to be applied. As a result, conventional plating systems of the past had to be manufactured in many different lengths and spacing configurations which were nevertheless fixed in an attempt to provide plates for many, though still possibly not all, of the various sizes and spacings of the vertebral bodies to which the plate was to be applied. For example, in a multi-segment plate the length of the plate would need to correspond to the overall length of the vertebral bodies to be joined and the actual distances therebetween; and the screw holes of the plate arranged to overlie the vertebral bodies. In order to cover the possible range of sizes, health care facilities would need to carry a large inventory of different sized plates. In some cases as many as sixty different sized plates would be needed. Such a large inventory is an expensive undertaking and still worse, facilities with a high caseload need to invest in more than one of each plate size to provide for the possibility of overlapping demand for the same plate size. Facilities with lower caseloads may find it prohibitively expensive to stock an inventory of plates sufficient to cover the range of possible sizes, and thus, might not be able to afford to stock a set at all or have less than all sizes of plates needed for all cases. Manufactures cannot afford to place a set of plates on consignment in facilities with low caseloads as the number of sales would not cover the carrying costs of the plates.

There exists therefore a need for an improved anterior cervical plating system that (1) allows for the creation of a variety of lengths of the overall plating system construct; (2) allows for variations in spacing between the bone screw receiving holes corresponding to the attachment points of the plating system to each of the vertebral bodies, respectively; and (3) reduces the requisite plate inventory.

It is known in the art that compressive load, within a physiological range across a fusion site, is beneficial to the fusion process. Conversely, a failure to maintain a compressive load across a fusion site, or to have a gap in the fusion construct continuity may lead to a failure to achieve fusion called pseudoarthrosis. A primary purpose of cervical hardware is to provide stability during the healing and fusion process. The fusion process occurs in part through a process called "creeping substitution" by which new living bone replaces the dead bone such as that of a bone graft. The fusion process involves a phase of bone resorption as preliminary to the formation of the new bone. It is possible then for the bone resorption to result in gaps in the continuity of the fusion mass, such that if the hardware is sufficiently rigid, such as occurs as a result of increasing the strength of the components and constraining the relationship of the screws to the plate, those gaps may persist and increase in size as the hardware holds the bone parts separated rather than allowing those bone parts to move together to close those gaps. This holding apart of the bone parts called distraction can therefore lead to a failure of fusion called distraction pseudoarthrosis.

Alternative cervical plating systems have attempted to prevent distraction pseudoarthrosis by allowing the vertebral bodies to collapse towards each other as needed during the fusion process. Generally this has been done by allowing the bone screws to be free to move relative to the plate, that is, movement such as sliding, swiveling, rotating, and angulating, independent of whether the screws are prevented from separating or backing out of the plates such as by the use of locks. Undesired multidirectional instability can occur in such plating systems that is counter to the very purpose of such hardware which is to increase or provide for stability.

Another approach to solving this problem has been to attach by screws a block to each of the vertebral bodies to be fused and then to allow those blocks to slide up and down on a pair of rods. Each of these constructs have in common that they sacrifice stability, the ability to hold the bones to be fused rigidly in place and to prevent undesired motion; for the ability to allow, but not cause the vertebral bodies to collapse.

There exists therefore a need for an improved anterior cervical plating system that is: (1) sufficiently rigid to maintain the desired alignment of the vertebral bodies to be fused; (2) capable of inducing compressive load across the fusion site; (3) capable of allowing for the motion of the vertebral bodies towards each other to prevent or to close any gaps in the continuity of the fusion construct, while still being capable of preventing motion in all other directions; and/or (4) can avoid or prevent distraction pseudoarthrosis without itself introducing multidirectional instability.

SUMMARY OF THE INVENTION

The present invention is an anterior cervical plating system comprising vertebral body engaging anchors coupled to a connecting plate in moveable relationship to vary the spacing between anchoring points of the plating system to the vertebral bodies; to create and/or store a compressive load across a disc space between two adjacent vertebral bodies to be fused; and/or to allow motion of the vertebral bodies toward each other to prevent or close gaps in the continuity of a fusion construct, while preferably preventing motion in all other directions when in use.

As used herein, a spinal fusion segment is defined as two adjacent vertebral bodies with an intervertebral implant, made of bone or an artificial material, in the disc space therebetween. As used herein, a fusion construct is defined as a spinal fusion segment plus the hardware, such as a connecting plate, vertebral body engaging anchors, and screws for example.

The vertebral body engaging anchors can be moved to vary the spacing therebetween so that the plating system may be adjusted to correspond to a range of sizes and spacing of the adjacent vertebral bodies to which the plating system is being applied, thereby greatly reducing the inventory needed. Each vertebral body engaging anchor is attached to a vertebral body to be fused by at least one bone screw and preferably a pair of bone screws, which when inserted, are preferably prevented from unwanted loosening and backing out by at least one lock. Each of the vertebral body engaging anchors can be positioned on vertebral bodies, respectively, to optimize bone screw positioning on the underlying vertebral bodies. The vertebral body engaging anchors are linked by a common connecting plate regardless of the spacing between the vertebral body engaging anchors.

The paths of the bone screws through the vertebral body engaging anchor may be fixed or variable. If the paths are variable, they may be made more or less stable depending on how resistant to motion the screws are relative to the vertebral body engaging anchor when the screws are locked. To the extent that screws are sufficiently stable in relation to the vertebral body engaging anchor to make use of the present inventive teaching, these screw, vertebral body engaging anchor, connecting plate, and lock combinations or variations thereon are also within the broad scope of the present invention.

In accordance with the purposes of the present invention, as embodied and broadly described herein, a plate system is provided for contacting the anterior aspects of at least two adjacent cervical vertebral bodies to be fused together. The plate system includes at least a first vertebral body engaging anchor adapted to be attached to one of the adjacent vertebral bodies to be fused and at least a second vertebral body engaging anchor adapted to be attached to another one of the adjacent vertebral bodies to be fused. Each of the first and second vertebral body engaging anchors has a lower facing surface adapted to contact one of the vertebral bodies, at least one upper facing surface opposite the lower facing surface, and at least one bone screw receiving hole extending from the at least one upper facing surface through the lower facing surface. Each of the bone screw receiving holes is adapted to overlie one of the vertebral bodies and receive at least one bone screw for engaging the vertebral body to attach a respective one of the at least first and second vertebral body engaging anchors to the cervical spine. Each of the first and second vertebral body engaging anchors has opposite sides and opposite ends adapted to be oriented along a longitudinal axis of the human spine.

The plate system also includes a connecting plate configured to connect the first and second vertebral body engaging anchors. The connecting plate is configured to overlap at least a portion of each of the first and second vertebral body engaging anchors, respectively. The connecting plate has a lower facing surface adapted to be oriented toward the vertebral bodies and an upper facing surface opposite the lower facing surface.

In a preferred embodiment, the plate system may include at least two fasteners, each of the fasteners being adapted to couple together the connecting plate and one each of the first and second vertebral body engaging anchors, respectively. The connecting plate preferably has at least one fastener receiving opening extending from the upper facing surface through the lower facing surface of the connecting plate. The fastener receiving opening is adapted to receive a fastener to attach the connecting plate to the first and second vertebral body engaging anchors. The connecting plate and at least one of the vertebral body engaging anchors may be configured to couple together.

In accordance with the purposes of a further embodiment of the present invention, as embodied and broadly described herein, a method of this invention is provided for stabilizing at least two adjacent vertebral bodies in the cervical human spine. The method includes the step of providing a plate system having at least a first and a second vertebral body engaging anchor adapted to be applied to the anterior aspects of a respective first and second vertebral body of an anterior human cervical spine. The plate system also has a connecting plate configured to connect the first and second vertebral body engaging anchors.

The method also includes the steps of inserting at least two bone screws through the first vertebral body engaging anchor of the plate system and into one of the vertebral bodies adjacent the disc space to be fused; inserting at least two bone screws through the second vertebral body engaging anchor and into the other of the vertebral bodies adjacent the disc space to be fused; connecting the first and second vertebral body engaging anchors with the connecting plate, the connecting plate overlapping at least a portion of each of the first and second vertebral body engaging anchors; and permitting movement of the first and second vertebral body engaging anchors attached to the adjacent vertebral bodies relative to the connecting plate and relative to one another.

The ability to permit the movement of adjacent vertebral bodies toward one another is referred to herein as "dynamization." Dynamization may be "passive" allowing the plating system to shorten the distance between its anchoring points to the vertebral bodies when a shortening force, such as a compressive load is applied. Dynamization may be "active" wherein the plating system stores energy to induce shortening of the fusion construct should the opportunity present itself. The present inventive plating system may passively dynamize, actively dynamize, provide a combination of both, as well as convert and store certain compressive stresses encountered during the healing phase as will be more fully described herein.

In a preferred embodiment of the present invention, after each of the vertebral body engaging anchors are attached to a respective one of the vertebral bodies to be fused and coupled to a connecting plate, the vertebral body engaging anchors are capable of movement along the connecting plate from a first or more separated position to a second or closer together position, a process generally referred to as "passive dynamization"—that is the ability of the system to allow the plated spinal segment to shorten in response to unmet compressive loads to allow for the bone portions to be fused to move closer together to maintain or restore contact. A preferred embodiment of this present invention is capable of allowing for this passive dynamization while preventing undesirable motions along and around all axes other than the motion along the longitudinal axis of the connecting plate.

In another preferred embodiment of the present invention, the vertebral body engaging anchors and the connecting plate are articulated in such a way that even the one freedom of movement that is along the longitudinal axis of the connecting plate is selectively limited to the desired passive dynamization—that is shortening of the plating system construct. This preferred embodiment of the present invention will shorten the distance between the vertebral body engaging anchors as required to maintain loaded contact of the bone portions to be fused, and if challenged, resist any forces such as those that would accompany cervical extension that would distract or destabilize the construct by elongating the distance between the vertebral body engaging anchors. A further benefit of this embodiment is its ability to store and impart a compressive load across the fusion site referred to herein as "active dynamization" wherein energy stored in the system shortens the distance between the vertebral body engaging anchors if conditions permit. This load can be applied by the surgeon at the time of surgery and/or be produced during the healing phase by harnessing the compressive loads such as occur randomly with neck motion. Compressive load within a physiological range has been shown to have a beneficial effect on the healing of bone. The induction of a compressive load across vertebral bodies to be fused, induces bone growth, and when bone resorption occurs at the interface of the graft or implant and the vertebral bodies to be joined, those vertebral bodies are urged to move closer together, thus avoiding the formation of a gap therebetween and thereby acting to mitigate against pseudoarthrosis.

Alternatively, various embodiments of the present invention allow the surgeon to induce a desired amount of preload (compressive force) across the fusion site and to permit a desired amount of shortening of the distance between the vertebral body engaging anchors—"active dynamization," should the opportunity occur; and yet lock the system to prevent any further shortening of that distance as might present a risk of deformity or be otherwise undesirable. Such a system urges the bone portions closer together.

In another preferred embodiment, a pre-load force can be applied to the vertebral body engaging anchors such that while the vertebral body engaging anchors may undergo no added motion initially, there is a selective force applied to the vertebral body engaging anchors and the vertebral body engaging anchors are capable of motion in only one direction, such that should resorption occur at one of the fusion interfaces then the vertebral body engaging anchors are not only free to move in a direction toward one another, and only in that direction, but are also urged to do so to relieve that preload force. Such a system urges the vertebral bodies together over time as resorption permits.

Alternatively, in another preferred embodiment of the plate of the present invention, a desired amount of preload (compressive force) may be induced across the fusion site to permit active dynamization should the opportunity occur, without locking the system such that after active dynamization is exhausted (if exhausted), then the plating system will still allow passive dynamization to occur thereafter. In another preferred embodiment, that passive dynamization is converted into active dynamization.

BRIEF DESCRIPTION OF THE DRAWINGS

FIG. 1 is a top plan view of a connecting plate in a first position, spaced apart vertebral body engaging anchors with bone screws installed, and fasteners to fasten the connecting plate to the vertebral body engaging anchors in accordance with a preferred embodiment of the present invention.

FIG. 2 is a top plan view of the connecting plate and vertebral body engaging anchors of FIG. 1 in a second position.

FIG. 3 is a side elevation view of the connecting plate, vertebral body engaging anchors, and bone screws of FIG. 1.

FIG. 4 is a top plan view of a vertebral body engaging anchor of FIG. 1 with optional surface ratchetings.

FIG. 8 is a bottom plan fragmentary view of the connecting plate with optional surface ratchetings and vertebral body engaging anchor of FIG. 1.

FIG. 9 is a top perspective fragmentary view of a portion of the connecting plate attached to an intermediate vertebral body engaging anchor and the fastener of FIG. 1.

FIG. 13 is a top plan view of the vertebral body engaging anchor and an instrument for positioning, aligning, and holding the vertebral body engaging anchor during installation in accordance with the present invention.

FIG. 14 is a cross sectional view of the instrument and vertebral body engaging anchor along line 14-14 of FIG. 13.

FIG. 21 is an exploded top plan view of a connecting plate and vertebral body engaging anchors adapted to be cooperatively engaged in a tongue and groove configuration in accordance with another preferred embodiment of the present invention.

FIG. 22 is a top plan view of the connecting plate and vertebral body engaging anchors of FIG. 21 in a cooperatively engaged position.

FIG. 23 is a cross sectional view along line 23-23 of FIG. 22.

DETAILED DESCRIPTION OF THE DRAWINGS

Figure 5:
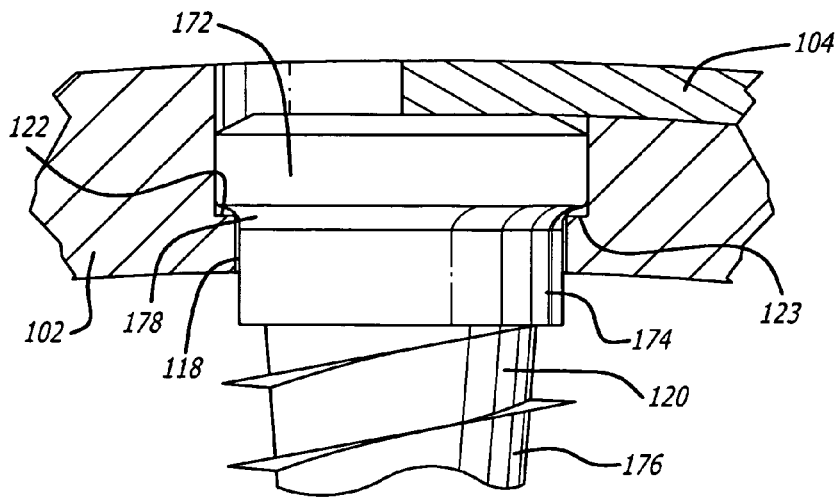
FIG. 5 is an enlarged fragmentary view along lines 5-5 of FIG. 2 with an embodiment of a bone screw being locked to the vertebral body engaging anchor in accordance with a preferred embodiment of the present invention.

The following description is intended to be representative only and not limiting and many variations can be anticipated according to these teachings, which are included within the scope of this inventive teaching. Reference will now be made in detail to the preferred embodiments of this invention, examples of which are illustrated in the accompanying drawings. Wherever possible, the same reference numbers will be used throughout the drawings to refer to the same or like parts.

FIGS. 1-4, 8, and 9 show a preferred embodiment of a cervical plating system 100 in accordance with the present invention. Plating system 100 preferably comprises a plurality of vertebral body engaging anchors 102 that are each adapted to overlie at least a portion of the anterior aspect of a vertebral body of the cervical spine and a connecting plate 104 adapted to couple together with vertebral body engaging anchors 102.

Vertebral body engaging anchors 102 each preferably have at least one upper facing surface 106, a lower facing surface 108 opposite upper facing surface 106 adapted to contact one of the vertebral bodies, a first end 110, a second end 112 opposite first end 110, and opposite sides 114, 116. Lower facing surface 108 of vertebral body engaging anchor 102 is preferably adapted to conform to the anterior aspect of at least a portion of a vertebral body of the cervical spine. For example, lower facing surface 108 may be at least in part concave along at least a portion of the longitudinal axis of the vertebral body engaging anchor, may be biconcave at least in part, that is, concave along the longitudinal axis of vertebral body engaging anchor 102 and concave transverse to the longitudinal axis of the vertebral body engaging anchor, or may have any shape suitable for the intended purpose transverse to the longitudinal axis of the vertebral body engaging anchor. A person skilled in the art will appreciate that vertebral body engaging anchor 102 may be adapted for other curvatures or have no curvature without departing from the intended purpose within the broad scope of the present invention.

If desired, at least a portion of lower facing surface 108 of vertebral body engaging anchor 102 may be configured to promote bone growth. For example only, lower facing surface 108 of vertebral body engaging anchor 102 may be roughened to promote the growth of bone therealong. Lower facing surface 108 of vertebral body engaging anchor 102 may also have a bone ingrowth surface if so desired.

As shown in FIGS. 1-3 and 9-10c, at least a portion of upper facing surface 106 of vertebral body engaging anchor 102 is preferably configured to cooperatively engage at least a portion of connecting plate 104 to couple vertebral body engaging anchor 102 to connecting plate 104. For example only, upper facing surface 106 of vertebral body engaging anchor 102 may be configured to have a recess 136 with an upper facing surface 138 and opposed sides 140, 142 adapted to retain at least a portion of connecting plate 104 therein. Opposed sides 140, 142 may be angled and recess 136 may be configured to form an interference fit with connecting plate 104. Recess 136 is preferably counter sunk to a depth sufficient to accommodate at least a portion of the height of connecting plate 104 therein. In a preferred embodiment, a portion 144 of upper facing surface 106 of vertebral body engaging anchor 102 lies approximately flush with at least a portion of an upper facing surface 124 of connecting plate 104 when connecting plate 104 is within recess 136 and coupled to vertebral body engaging anchor 102. Connecting plate 104 may snap fit into recess 136 to hold together vertebral body engaging anchors 102 and connecting plate 104. Alternatively, connecting plate 104 and vertebral body engaging anchors 102 may be configured to slideably engage one another. Sides 140, 142 of recess 136 are preferably configured to promote the coupling of vertebral body engaging anchors 102 to connecting plate 104, however, the invention is not so limited. For example, sides 140, 142 of recess 136 may be parallel to one another. In another preferred embodiment, vertebral body engaging anchors 102 and connecting plate 104 may couple together without any recess in the upper surface 106 of vertebral body engaging anchors 102.

Vertebral body engaging anchor 102 preferably has a thickness between upper facing surface 106 and lower facing surface 108 in the range of 1.5 mm to 3.5 mm, more preferably 2.0 mm to 3.0 mm. Preferably, the thickness of connecting plate 104 is less than the thickness of vertebral body engaging anchor 102. The width of vertebral body engaging anchor 102 is preferably greater than the width of connecting plate 104 adapted to be used therewith. The length of vertebral body engaging anchor 102 is preferably less than the height of a vertebral body to which vertebral body engaging anchor 102 is adapted to be attached to. The sides of vertebral body engaging anchor 102 may be angled relative to one another, for example, convergently angled, or may be parallel to one another. Within the plating system, the vertebral body engaging anchors may be interchangeable with one another. Preferably, but not necessarily, the vertebral body engaging anchors are identical to one another to reduce inventory and provide a cost savings benefit.

Vertebral body engaging anchors 102 are preferably configured to accommodate at least one bone screw receiving hole 118 extending from upper facing surface 106 through lower facing surface 108. For example only, first end 110 of vertebral body engaging anchor 102 may have a width that is greater than the width of second end 112 to accommodate a pair of bone screw receiving holes 118. Bone screw receiving holes 118 are preferably adapted to overlie one of the vertebral bodies and are adapted to receive at least one bone screw 120 for engaging the vertebral body to attach vertebral body engaging anchor 102 to a vertebral body. Bone screw receiving hole 118 is preferably configured to prevent the passage of a bone screw completely through vertebral body engaging anchor 102.

Figure 6:
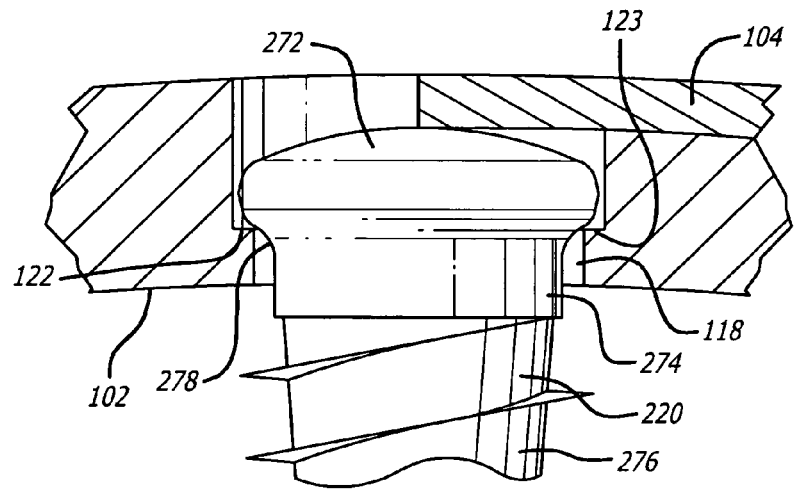
FIG. 6 is an enlarged fragmentary view along lines 5-5 of FIG. 2 with another embodiment of a bone screw being locked to the vertebral body engaging anchor in accordance with the present invention.
Figure 7:
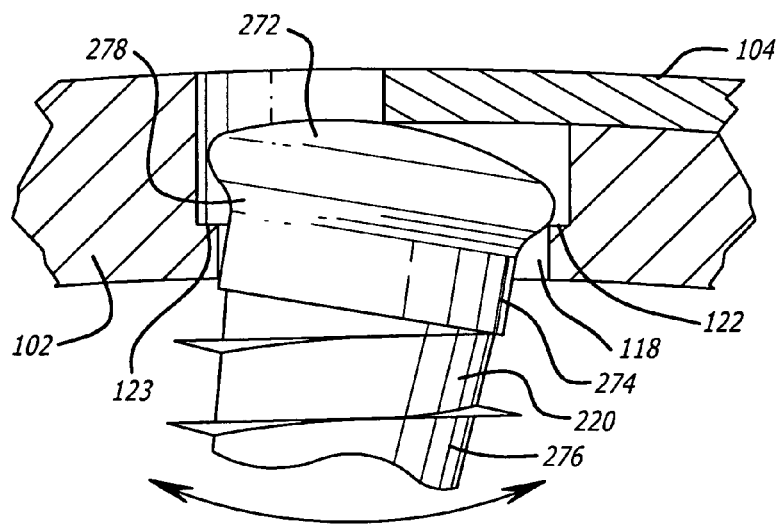
FIG. 7 is an enlarged fragmentary view along lines 5-5 of FIG. 2 with another embodiment of a bone screw being locked to the vertebral body engaging anchor and in moveable relationship to the vertebral body engaging anchor and connecting plate in accordance with the present invention.

As shown in FIGS. 5-7, by way of example only and not limitation, bone screw receiving hole 118 may have a reduced dimension proximate lower facing surface 108 of vertebral body engaging anchor 102 to form a seat 122. Seat 122 may have a surface 123 adapted to contact at least a portion of a bone screw inserted therein. Surface 123 may be at least in part planar, at least in part curved, or have any other configuration suitable for contacting at least a portion of a bone screw. Bone screw receiving hole 118 is preferably configured to receive a single bone screw, but may be configured to receive more than one bone screw if so desired. By way of example only and not limitation, a bone screw receiving hole may be in the form of a slot sized to receive at least two bone screws. Bone screw receiving holes 118 may be configured in a number of ways sufficient for the intended purpose. For example, bone screw receiving hole 118 and a bone screw may cooperate to form an interference fit with at least a portion of the trailing end of a properly dimensioned bone screw to be received therein. Bone screw receiving hole 118 and a bone screw may cooperate to hold the bone screw in fixed relationship to vertebral body engaging anchor 102, or may cooperate to allow the bone screw to be in a moveable relationship to vertebral body engaging anchor 102, as for example only, in a variable angular relationship, described below. It is appreciated that the same bone screw receiving hole can cooperate with bone screws of different configurations depending on whether a fixed or moveable relationship of the bone screw relative to vertebral body engaging anchor is desired. By way of example only and not limitation, a bone screw receiving hole may have a conical configuration and a bone screw having a tapered head with a corresponding shape may be inserted therein to form an interference fit with the bone screw receiving hole and be in fixed relationship thereto. Alternatively, a bone screw having a rounded head may be inserted into the same conical bone screw receiving hole to be in moveable relationship thereto and allow for variable angle positioning of the bone screw.

Vertebral body engaging anchors 102 and connecting plate 104 are configured to couple together. By way of example only and not limitation, vertebral body engaging anchors 102 and connecting plate 104 may be coupled together with a fastener, such as fastener 152 shown in FIG. 10a or fastener 252 shown in FIGS. 10b and 10c, or via a tongue and groove configuration such as shown in FIG. 21 and described in more detail below.

Figure 10A:
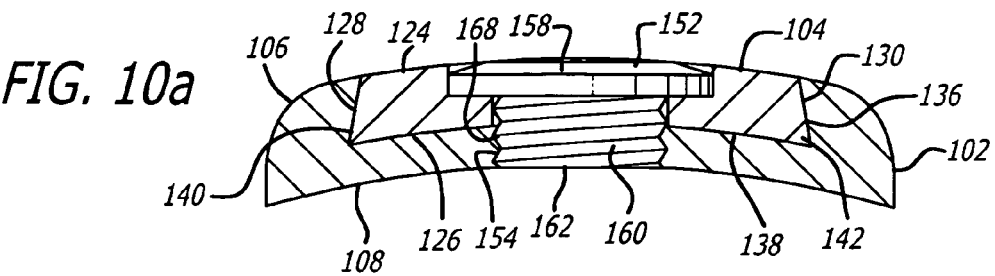
FIG. 10a is an enlarged cross sectional view along lines 10a-10a of FIG. 9 illustrating the fastener for attaching the connecting plate to an intermediate vertebral body engaging anchor.

When vertebral body engaging anchors 102 and connecting plate 104 are coupled together with fasteners, vertebral body engaging anchors 102 may each include a fastener receiving opening. For example, FIGS. 4 and 10a show a fastener receiving opening 154 extending from upper facing surface 106 through lower facing surface 108 for receiving a portion of fastener 152, described in more detail below. Where the fastener has a thread, fastener receiving opening 154 of vertebral body engaging anchor 102, for example, may be configured to have a thread 168 adapted to engage with the thread of the fastener. The threaded engagement of the fastener to fastener receiving opening 154 permits connecting plate 104 and vertebral body engaging anchor 102 to be coupled to each other.

As shown in FIGS. 1-3 and 9, connecting plate 104 has an upper facing surface 124, a lower facing surface 126 opposite upper facing surface 124 adapted to be oriented toward the vertebral bodies and contact at least a portion of upper facing surface 106 of vertebral body engaging anchor 102, opposed sides 128, 130, and opposed ends 132, 134. Upper facing surface 124 and lower facing surface 126 of connecting plate 104 are preferably, though need not be configured to generally match the natural curvature of the human spine. Sides 128, 130 of connecting plate 104 may be configured to cooperatively engage the sides of recess 136 of vertebral body engaging anchors 102. For example, sides 128, 130 of connecting plate 104 may be angled so that connecting plate 104 proximate upper facing surface 124 has a width less than the width of connecting plate 104 proximate lower facing surface 126 to correspond to the shape of recess 136.

Figure 18:
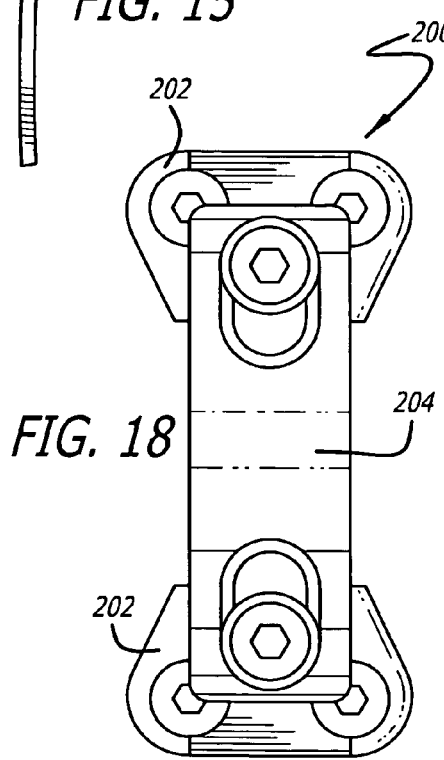
FIG. 18 is a top plan view of a connecting plate in a first position, spaced apart vertebral body engaging anchors with bone screws installed, and fasteners to fasten the connecting plate to the vertebral body engaging anchors in accordance with another preferred embodiment of the present invention.
Figure 19:
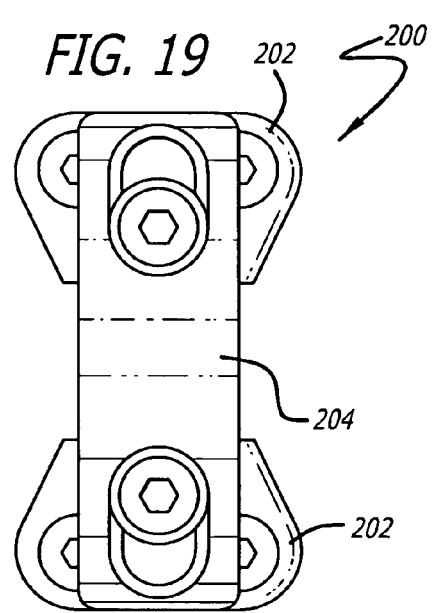
FIG. 19 is a top plan view of the connecting plate and vertebral body engaging anchors of FIG. 18 in a second position.

Connecting plate 104 has a length along a longitudinal axis L that is preferably sufficient to overlap at least a portion of two or more adjacent vertebral bodies and span the disc space(s) therebetween. It will be appreciated that the plating system of the present invention may be adapted to span any number of adjacent vertebral bodies and still remain within the broad scope of the present invention. For example, FIGS. 18 and 19 show a plating system 200 having a connecting plate 204 similar to connecting plate 104 except that it is configured for use across a single disc space and to overlap at least a portion of two adjacent vertebral bodies of the cervical spine.

When vertebral body engaging anchors 102 and connecting plate 104 are coupled together with fasteners, connecting plate 104 may include at least one fastener receiving opening 156 extending from upper facing surface 124 through lower facing surface 126 of connecting plate 104 that is adapted to receive fastener 152. As shown in FIGS. 1 and 2, fastener receiving opening 156 of connecting plate 104 is preferably configured to permit selected movement of fastener 152 therein and to permit selected motion of vertebral body engaging anchor 102 and connecting plate 104 along the longitudinal axis of connecting plate 104. For example, fastener receiving opening 156 may be oval-shaped, or any other shape suitable for the intended purpose of permitting movement of vertebral body engaging anchor 102 relative to connecting plate 104 along the longitudinal axis of connecting plate 104. Fastener receiving opening 156 may be configured to prevent the head of fastener 152 from passing therethrough. For example, fastener receiving opening 156 of connecting plate 104 may include a shoulder 170 recessed from upper facing surface 124 of connecting plate 104 adapted to contact the underside of the head of fastener 152.

As shown for example in FIGS. 1, 2, 9, and 10a, in a preferred embodiment where fasteners are used, fastener 152 is configured to couple together connecting plate 102 and at least one vertebral body engaging anchor 104 to limit their separation. As shown in FIG. 10a, fastener 152 may be embodied in the form of a screw having a head 158, a shaft 160, and a thread 162. In a first position, fastener 152 may be less than fully tightened to connecting plate 104 to permit movement of vertebral body engaging anchors 102 relative to connecting plate 104 along the longitudinal axis of connecting plate 104 as well as along an axis transverse to the longitudinal axis of connecting plate 104. Fastener 152 can be tightened to another position to limit movement of connecting plate 104 and vertebral body engaging anchors 102 relative to one another in at least one direction along the longitudinal axis of connecting plate 104.

Figure 10B:
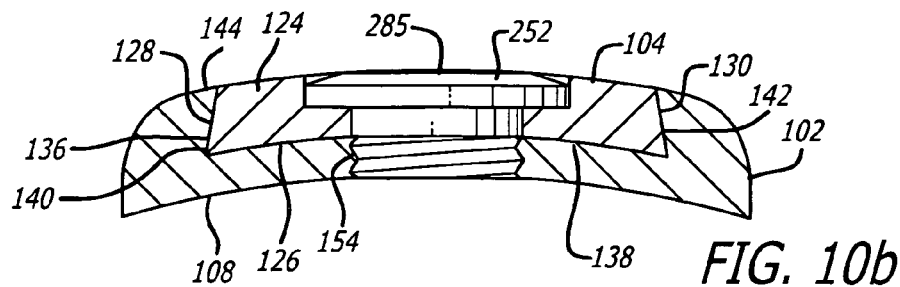
FIG. 10b is an enlarged cross sectional view along lines 10a-10a of FIG. 9 with another embodiment of a fastener for attaching the connecting plate to the vertebral body engaging anchor and permitting a desired amount of movement of the connecting plate and vertebral body engaging anchor relative to one another in accordance with the present invention.
Figure 10C:
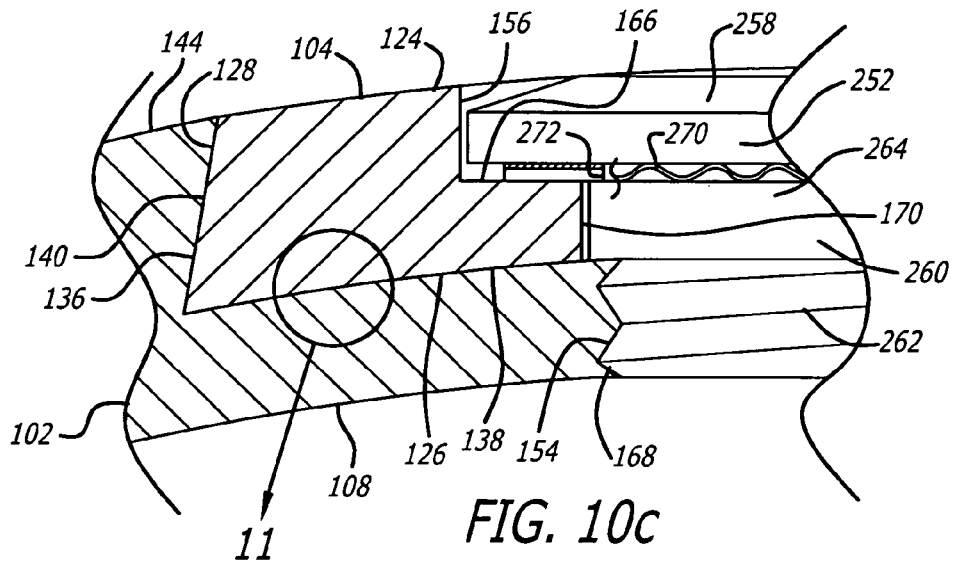
FIG. 10c is an enlarged fragmentary view of FIG. 10b.

FIGS. 10b and 10c show another preferred embodiment a fastener configured to permit movement of connecting plate 104 relative to at least one vertebral body engaging anchor 102 even when fully tightened. Fastener 252 may be configured to be tightened to only one of connecting plate 104 and vertebral body engaging anchor 102 so as to permit movement of vertebral body engaging anchor 102 and connecting plate 104 relative to one another. For example, fastener 252 may have a shoulder 264 adapted to bear upon vertebral body engaging anchor 102. Shoulder 264 is dimensioned so as to create a gap 166 between head 258 and connecting plate 104 so as to still permit a specific and desired motion of vertebral body engaging anchor 102 and connecting plate 104 relative to one another when fastener 252 is fully tightened.

The fastener may be locked to prevent its backing out from either or both of fastener receiving openings 154, 156. For example only, connecting plate 104 may include a fastener locking element adapted to lock at least one fastener to the connecting plate if so desired. Such a locking element may include a ring configured to be placed at least in part within fastener receiving opening 156 of connecting plate 104. The fastener locking element may alternatively be configured to cover at least a portion of one or more fasteners, for example, in a manner similar to that described relative to bone screws by Michelson in U.S. Pat. No. 6,139,550 (the '550 patent), the disclosure of which is incorporated by reference herein.

It is appreciated that fasteners are not required to couple together vertebral body engaging anchors 102 to connecting plate 104. Other methods, devices, and/or configurations of the vertebral body engaging anchors and connecting plate may be used to couple together vertebral body engaging anchors 102 and connecting plate 104.

By way of example, FIGS. 21-23 show another preferred embodiment of vertebral body engaging anchor 602 and connecting plate 604 coupled together in a tongue and groove configuration. By way of example, connecting plate 604 may have a portion with a cross section transverse to the longitudinal axis of connecting plate 604 that is C-shaped forming grooves 680. Connecting plate 604 has at least one tab 682 along each of its sides. Preferably, a plurality of tabs 682 are spaced apart along the sides of connecting plate 604. Vertebral body engaging anchors 602 may have a portion with a cross section transverse to the longitudinal axis of vertebral body engaging anchor 602 that is T-shaped forming sides 684. Vertebral body engaging anchor 602 is adapted to cooperatively engage the C-shaped cross section of connecting plate 604 so that sides 684 engage grooves 680, respectively. Sides 684 of vertebral body engaging anchors 602 include notches 686 configured to permit at least one tab 682 of connecting plate 604 to pass therethrough. In use, connecting plate 604 is positioned over vertebral body engaging anchors 602 so that tabs 682 align with corresponding notches 686 to slideably engage sides 684 with grooves 680 to couple together vertebral body engaging anchor 602 and connecting plate 604. It is appreciated that the vertebral body engaging anchors and the connecting plate may be configured so that at least one of the vertebral body engaging anchors may have a portion configured as a tongue with a cross section adapted to be received in a groove of the connecting plate.

Preferably at least a portion of connecting plate 104 is configured to interdigitate with at least a portion of at least one of vertebral body engaging anchors 102 to permit the adjacent vertebral bodies to "dynamize," or move toward one another after the vertebral body engaging anchor is attached to the vertebral body and connected by a connecting plate. Dynamization may be "passive" allowing the distance between the vertebral body engaging anchors to shorten when a shortening force, such as a compressive load, is applied. Dynamization may be "active" whereby the plating system stores energy to induce shortening of the overall plating system construct. The plating system of the present invention may passively dynamize, actively dynamize, provide a combination of both, as well as convert and store certain compressive stresses encountered during the healing phase as will be more fully described below.

For example only, as shown in FIGS. 4, 8, 11, and 12, at least a portion of lower facing surface 126 of connecting plate 104 and at least a portion of upper facing surface 106 of vertebral body engaging anchor 102 may include a surface configuration, such as ratchetings 146 configured to cooperatively interdigitate to permit selected and sequential movement along the longitudinal axis of connecting plate 104. The ratchetings are preferably biased to allow movement in one preferred direction along the longitudinal axis of the connecting plate so as to allow movement of vertebral body engaging anchors 102 toward one another in a first direction along the longitudinal axis of connecting plate 104 and to resist movement in a direction opposite to the first direction.

Figure 11:
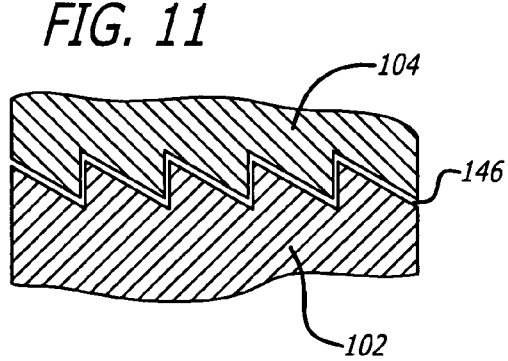
FIG. 11 is enlarged fragmentary view along line 11 of FIG. 10c illustrating a preferred embodiment of surface ratchetings in a first position in accordance with the present invention.
Figure 12:
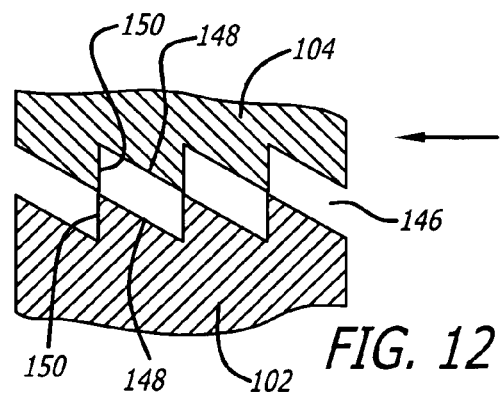
FIG. 12 is enlarged fragmentary view along line 11 of FIG. 10c illustrating a preferred embodiment of the surface ratchetings in a second position in accordance with the present invention.

FIGS. 11 and 12 show a preferred embodiment of ratchetings 146 having a forward-facing configuration for permitting movement in a single direction. The configuration of ratchetings 146 is useful when movement of vertebral body engaging anchors 102 toward one another is desired to permit further shortening of the distance between vertebral body engaging anchors 102. A preferred angular relationship of the triangular cross section of ratchetings 146 is a 30-60-90 degree triangular relationship. As shown in FIG. 12, due to the forward facing angle of ratchetings 146, sliding movement of vertebral body engaging anchor 102 and connecting plate 104 in the direction, as indicated by the arrow, along the longitudinal axis of connecting plate 104 is facilitated by a ramped surface 148. In contrast, sliding movement in the opposite direction is restricted by a vertical wall 150. Movement of vertebral body engaging anchor 102 and connecting plate 104 is limited to a single direction with ratchetings 146 and by limiting the separation of vertebral body engaging anchor 102 and connecting plate 104 along an axis transverse to the longitudinal axis of connecting plate 104.

In order for vertebral body engaging anchors 102 and connecting plate 104 to move relative to one another, there should be sufficient freedom of movement for connecting plate 104 and vertebral body engaging anchors 102 to move apart in order to clear the height of the peaks of ratchetings 146. One way to achieve this freedom of movement includes coupling together vertebral body engaging anchors 102 and connecting plate 104, such as for example in the tongue and groove configuration described above, with sufficient spacing between the tongue and groove to allow connecting plate 104 and vertebral body engaging anchors 102 to move apart to clear the peaks of ratchetings 146. Vertebral body engaging anchors 102 and connecting plate 104 may have slightly different longitudinal curvatures to spring apart vertebral body engaging anchors 102 and connecting plate 104 when coupled together. For example only, the radius of curvature of lower surface 126 of connecting plate 104 may be different from the radius of curvature of upper surface 106 of vertebral body engaging anchors 102.

Another way to achieve sufficient freedom of movement for connecting plate 104 and vertebral body engaging anchors 102 to move apart in order to clear the height of the peaks of ratchetings 146 includes the use of at least one fastener to couple and selectively tighten together vertebral body engaging anchors 102 and connecting plate 104. For example only, fastener 152 may be less than fully tightened to connecting plate 104 to permit movement of vertebral body engaging anchors 102 and connecting plate 104 along the longitudinal axis of connecting plate 104 as well as along an axis transverse to the longitudinal axis of connecting plate 104 such that ratchetings 146 can move apart. Fastener 152 may then be tightened to another position to resist or otherwise limit movement of connecting plate 104 and vertebral body engaging anchors 102 relative to one another in at least one direction along the longitudinal axis of connecting plate 104 using, for example only, the shape of fastener receiving opening 156 of connecting plate 104.

For example, fastener 152 may be tightened to a first position adapted to facilitate movement of at least two vertebral body engaging anchors 102 relative to connecting plate 104 in a direction toward one another along the longitudinal axis of connecting plate 104 and to resist or limit the movement of at least two vertebral body engaging anchors 102 away from one another along the longitudinal axis of connecting plate 104. Therefore, the distance between two vertebral body engaging anchors 102 can be shortened if the distance between the two adjacent vertebral bodies decreases, even after connecting plate 104 is installed, so that the vertebral bodies are not held apart by connecting plate 104 and vertebral body engaging anchors 102, to prevent the occurrence of pseudoarthrosis.

In a preferred embodiment of the present invention, it may be desirable to apply a spring force to control separation of connecting plate 104 from at least one of vertebral body engaging anchors 102 to resist movement of vertebral body engaging anchors 102 away from one another along connecting plate 104. As shown in FIG. 10c, by way of example, fastener 252 may be used with a spring washer 270 configured to be positioned between head 258 of fastener 252 to apply spring pressure to connecting plate 104. Spring washer 270 may be held in a groove 272 formed in the lower portion of head 258 of fastener 252.

As another example, the head of fastener 252 may be configured to apply a spring force to control separation of connecting plate 104 from at least one of vertebral body engaging anchors 102. For example, at least a portion of the lower surface of the head of fastener 252 adapted to contact connecting plate 104 may be flexible, concave, and/or may have a configuration similar to spring washer 270.

In another example, the curvature of a lower facing surface of connecting plate 104 and the curvature of an upper facing surface of vertebral body engaging anchors 102 may be slightly different. The different curvatures cooperate with one another to resist connecting plate 104 and vertebral body engaging anchors 102 from moving apart.

It will be understood by those skilled in the art that other ways exist to achieve sufficient freedom of movement for connecting plate 104 and vertebral body engaging anchors 102 to move apart relative to one another while remaining coupled together and are within the broad scope of the present invention.

If active dynamization is desired, the forward-facing configuration of ratchetings 146 may be used to store and maintain a compressive load across a disc space between the adjacent vertebral bodies. The compressive load stored may be applied by the surgeon and/or compressive loads that occur randomly with neck motion during the healing phase. For example, the surgeon may induce a desired amount of "preload," or compressive force across the fusion site after plate attachment by moving two or more vertebral body engaging anchors 102 toward one another to shorten the length of the over-all construct of the plating system as desired. Inducing a preload enhances fusion by maintaining a compressive force between adjacent vertebral bodies and reducing the chance that gaps might develop as new living bone replaces the dead bone during the fusion process.

Figure 20:
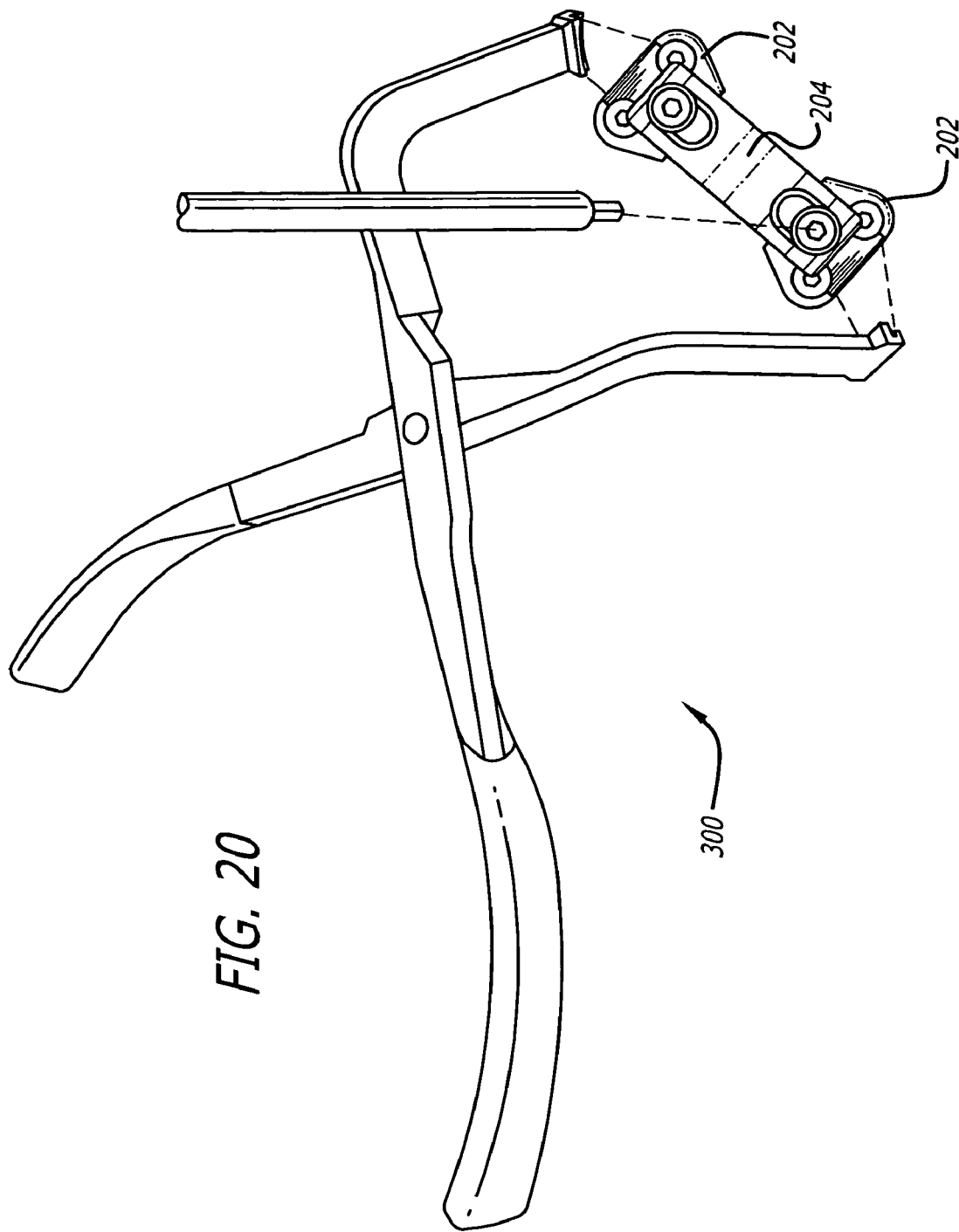
FIG. 20 is a perspective view of a preferred embodiment of a compression instrument for use with the vertebral body engaging anchors and connecting plate of the present invention.

As shown in FIG. 20, the vertebral body engaging anchors may, by way of example only and not limitation, be configured to cooperatively engage a compression instrument 300 in order to induce a compressive force across the fusion site. Compression instrument 300 may be used to move vertebral body engaging anchors 102 attached to adjacent vertebral bodies, respectively, toward one another to apply a compressive load across the disc space to be fused. Once a compressive load has been applied, connecting plate 104 may be sufficiently tightened to vertebral body engaging anchors 102 so that vertebral body engaging anchors 102 may, if desired, only move toward one other along the longitudinal axis of connecting plate 104, or further tightened to prevent any movement of vertebral body engaging anchors 102 relative to connecting plate 104.

Alternatively, connecting plate 104 and/or vertebral body engaging anchor 102 may, for example, include further openings therein configured to permit at least a portion of a compression instrument to pass through connecting plate 104 and engage the underlying vertebral body such as taught by Michelson in U.S. Pat. No. 6,193,721 (the '721 patent), incorporated by reference herein.

In another preferred embodiment of the present invention, the plating system need not provide for dynamization. For example, if no movement of connecting plate 104 and vertebral body engaging anchors 102 is desired after fastener 152 is tightened, the ratchetings may be configured in a 45-45-90 degree triangular relationship. Accordingly, fastener 152 can be tightened to a second position to completely restrict movement of connecting plate 104 and vertebral body engaging anchors 102 relative to one another along at least a portion of the longitudinal axis of connecting plate 104.

Bone screws may be locked to the vertebral body engaging anchor to prevent unwanted loosening and backing out from the bone screw receiving holes if so desired, for example, by physically blocking the bone screw to prevent backing out. For example only, as shown in FIGS. 1, 2, 5-7, and 9, a portion of connecting plate 104, when coupled to vertebral body engaging anchors 102, may be configured to cover at least a portion of at least one of bone screw receiving holes 118 and may cover at least a portion of a bone screw 120 inserted therein. Where bone screw receiving holes 118 are oriented side-by-side such as shown in FIG. 9, connecting plate 104 may be configured to cover at least a portion of a pair of bone screw receiving holes 118 to lock bone screws 120 therein. For example, connecting plate 104 may cover bone screw receiving holes 118 by sliding or snapping into recess 136 of vertebral body engaging anchor 102 to cover at least a portion of one or more bone screw receiving holes such as shown in FIGS. 9-10c.

Other methods, devices, and/or configurations exist to lock bone screws and are within the broad scope of the present invention. For example, where it is desired to lock only a single one of the bone screws to one of vertebral body engaging anchors 102, suitable bone screw locks may exist in the form of a screw, a rivet, a cap, or a cover. It is appreciated that any locking element for locking a single one of the bone screws known to one of ordinary skill in the art would be within the scope of the present invention. Alternatively, multi-lock bone screw locks may be used to lock at least two bone screws to a single vertebral body engaging anchor 102 if so desired. Examples of single-lock bone screw locks and multi-lock bone screw locks are taught by Michelson in the '550 patent and may be used to prevent a single bone screw or a plurality of bone screws from backing out from corresponding bone screw receiving hole once inserted therein.

FIGS. 5-7 show examples of bone screws usable with the present invention. The bone screws may be configured for fixed or moveable engagement within each bone screw receiving hole. It is appreciated that the same bone screw receiving hole can cooperate with bone screws of different configurations depending on whether a fixed or moveable relationship of the bone screw relative to vertebral body engaging anchor is desired. By way of example only and not limitation, FIG. 5 shows bone screw 120 having a head 172, a shoulder 174 proximate head 172, and a shaft 176 having a leading end adapted for insertion into the cervical spine. Head 172 is preferably configured to be in a fixed relationship to at least one of vertebral body engaging anchors 102. For example, the top of head 172 may be configured to be generally planar so that when covered by a portion of connecting plate 102 or other bone screw lock, for example, connecting plate 102 prevents substantial movement of bone screw 120 within bone screw receiving hole 118. The vertical side wall of bone screw receiving hole 118 cooperates with the vertical side wall of head 172 to create an interference fit. A junction 178 between head 172 and shoulder 174 may be generally squared.

As shown in FIGS. 6 and 7, the vertebral body engaging anchors of present invention may include a bone screw system that allows the vertebrae to move toward an interposed fusion construct such as a bone graft, and each other if necessary, instead of keeping the vertebrae apart during the occurrence of the resorption phase of the creeping substitution process. For example, a bone screw 220 may include a head 272 having a generally rounded top portion configured to permit bone screw 220 to move within bone screw receiving hole 118 when a lock such as connecting plate 104 or other lock covers the bone screw. Bone screw 220 may also include a junction 278 between head 272 and shoulder 274 that is generally rounded to permit bone screw 220 to be in moveable relationship, for example, variable angular relationship, relative to bone screw receiving hole 118 of at least one of vertebral body engaging anchors 102. Other screwplate-lock systems may be used and are within the broad scope of the present invention. For example, the '550 patent discloses three types of screw-plate-lock systems, which are themselves combinable with one another, as follows: (1) Passive Dynamic; (2) Self-Compressing; and (3) Active Dynamic.

FIGS. 13 and 14 show a preferred embodiment of an alignment instrument for positioning, aligning, and/or holding the vertebral body engaging anchor during installation in accordance with the present invention, generally referred to by the number 400. Alignment instrument 400 is preferably used to apply the plate system of the present invention to three or more adjacent vertebral bodies and across the disc spaces therebetween. Alignment instrument 400 includes an upper facing surface 402, a lower facing surface 404, a leading end 406, and opposed sides 408, 410. In a preferred embodiment, extending from upper facing surface 402 is a handle 430 for use in positioning and holding the alignment instrument in a desired position. Alignment instrument 400 is preferably configured to cooperatively engage at least one vertebral engaging anchor 102. For example, lower facing surface 404 may preferably include an engagement peg 412 sized and configured to fit into fastener receiving opening 154 of vertebral body engaging anchor 102. Engagement peg 412 may be configured to have a plurality of resilient portions 414 biased outward from the central longitudinal axis of engagement peg 412 to grab and hold vertebral body engaging anchor 102 while seated in fastener receiving opening 154 of vertebral body engaging anchor 102.

Opposed sides 408, 410 preferably have a contour along at least a portion of the length of each side that is configured to permit the insertion of a bone screw into a bone screw receiving hole while alignment instrument 400 is engaged with vertebral body engaging anchor 102. For example, each side 408, 410 may have an arcuate section 416 configured to substantially correspond to the perimeter of a bone screw receiving hole when alignment instrument 400 is engaged to vertebral body engaging anchor 102. Each arcuate section 416 is preferably positioned along a portion of the length of each side 408, 410 so that the distance between the central longitudinal axis of engagement peg 412 and leading end 406 is less than the distance between the mid-point of each arcuate section 416 and leading end 406. Such a configuration is suitable, for example, when leading end 406 is adapted to face second end 112 of vertebral body engaging anchor 102.

Alignment instrument 400 may be used to place and align a plurality of vertebral body engaging anchor 102 in a desired position on respective vertebral bodies to be fused. For example, alignment instrument 400 may be used to place a first vertebral body engaging anchor 102 on a first vertebral body. Alignment instrument 400 may be used to place a second vertebral body engaging anchor 102 on a vertebral body adjacent the first vertebral body. Alignment instrument 400 may be used to align the second vertebral body engaging anchor 102 with the first vertebral body engaging anchor 102 to be able to line up with connecting plate 104.

Holes can be formed in the vertebral bodies through bone screw receiving holes 118 of each vertebral body engaging anchor 102 while being held on the respective vertebral bodies by alignment instrument 400. Bone screws 120 can then be inserted into bone screw receiving holes 118 to secure each vertebral body engaging anchor 102 to the respective vertebral body. Preferably, the first vertebral body engaging anchor 102 may be secured to the first vertebral body before placing and aligning the second vertebral body engaging anchor on the other vertebral body. Alignment instrument 400 is removed from the vertebral body engaging anchor and connecting plate 104 is positioned over the vertebral body engaging anchors. The connecting plate is coupled to each vertebral body engaging anchor, preferably using one of the above-described methods and/or configurations of vertebral body engaging anchors and connecting plates for coupling together the vertebral body engaging anchors and the connecting plate. If it is desired to preload the plating system, a compressive load may be applied across the fusion site by a suitable compression instrument such as compression instrument 300. Connecting plate 104 may then be sufficiently tightened to vertebral body engaging anchors 102 so that vertebral body engaging anchors 102 may, for example, only move toward one other along the longitudinal axis of connecting plate 104, or further tightened to prevent any movement of vertebral body engaging anchors 102 relative to connecting plate 104.

Any instrument capable of engaging the connecting plate so as to serve the intended purpose would be within the scope of the instrumentation and method of the present invention. As an example only, methods and instrumentation for installing plates to the cervical spine, including a pilot hole forming punch to create bone screw receiving holes in the vertebral bodies coaxially aligned with the bone screw receiving holes with the plate, are taught and described by Michelson in the '721 patent.

Figure 17:
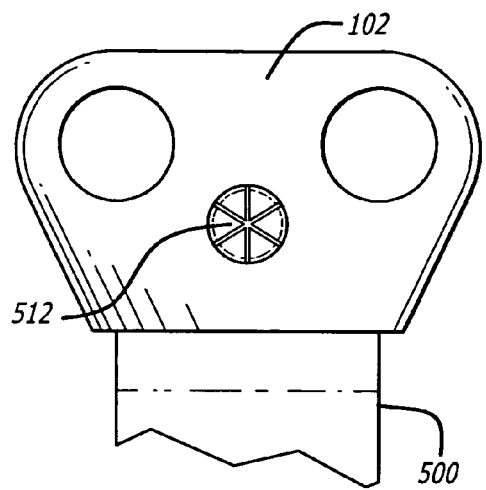
FIG. 17 is a fragmentary bottom plan view along lines 17-17 of FIG. 15.
Figure 16:
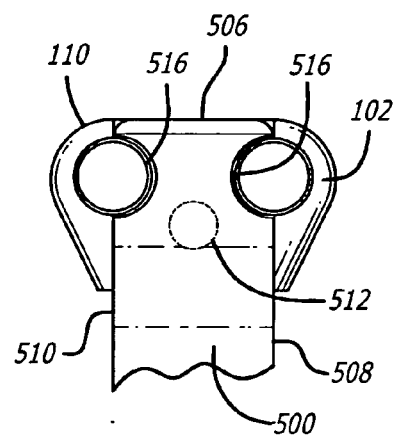
FIG. 16 is a fragmentary top plan view of the instrument and vertebral body engaging anchor of FIG. 15.
Figure 15:
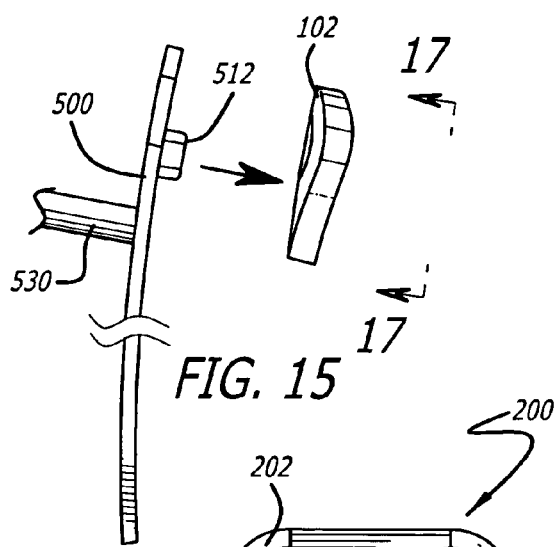
FIG. 15 is an exploded side elevation view of the vertebral body engaging anchor and another embodiment of an instrument for positioning, aligning and holding the vertebral body engaging anchor during installation in accordance with the present invention.

FIGS. 15-17 show another preferred embodiment of an alignment instrument for positioning, aligning, and holding the vertebral body engaging anchor during installation in accordance with the present invention, generally referred to by the number 500. Alignment instrument 500 is similar to alignment instrument 400 and is preferably used to apply the plate system of the present invention to two adjacent vertebral bodies and across a disc space therebetween. In a preferred embodiment, extending from upper facing surface 502 is a handle 530 for use in positioning and holding the alignment instrument in a desired position. Alignment instrument 500 preferably has each arcuate section 516 positioned along the length of each side 508, 510 so that distance between the central longitudinal axis of engagement peg 512 and leading end 506 is greater than the distance between the mid-point of each arcuate section 516 and leading end 506. Such a configuration is suitable, for example, when leading end 506 is adapted to face first end 110 of vertebral body engaging anchor 102. It is appreciated that other instruments for aligning, position, and holding vertebral body engaging anchors 102 are possible and within the broad scope of the present invention. By way of example and not limitation, such instruments are taught by Michelson in the '721 and '550 patents, incorporated herein by reference.

Preferred embodiments of the present invention have been described above in relation to a preferred use in the anterior cervical spine. It is appreciated that the present invention may be used in the thoracic spine or the lumbar spine, anteriorly.

It is appreciated that for any of the embodiments of the plating system described herein can be made of, treated, coated, combined with, comprised of, or used with any source of osteogenesis, fusion promoting substance, bone growth promoting materials, bone derived substances or products, demineralized bone matrix, mineralizing proteins, ossifying proteins, bone morphogenetic proteins, hydroxyapatite, genes coding for the production of bone, a substance at least in part other than bone, and bone including, but not limited to, cortical bone. The vertebral body engaging anchors, connecting plates, screws, fasteners, and/or screw locks may also be combined with material for inhibiting scar formation. The vertebral body engaging anchors, connecting plates, screws, fasteners, and/or screw locks may be combined with or comprise an antimicrobial material and/or surface treated or coated to be antibacterial, such as for example, by a silver coating. At least a portion of the bottom surface of the vertebral body engaging anchors can preferably have a porous, and/or textured surface and may be coated with, impregnated with, or comprise of fusion promoting substances (such as bone morphogenetic proteins) so as to encourage the growth of bone along the underside of the plate from bone portion to bone portion. The textured bottom surface also provides a medium for retaining fusion promoting substances with which the bottom surface layer can be impregnated prior to installation. The bottom surface of the vertebral body engaging anchors may be given the desired porous textured form by rough blasting or any other conventional technology, such as etching, plasma spraying, sintering, and casting for example. If porous so as to promote bone ingrowth, the bottom surface is formed to have a porosity or pore size in the order of 50-500 microns, and preferably 100-300 microns. Bone growth promoting substances with which the porous, textured bottom surface can be impregnated include, but are not limited to, bone morphogenetic proteins, hydroxyapatite, or hydroxyapatite tricalcium phosphate. The vertebral body engaging anchors, connecting plate, screws, fasteners, and/or bone screw locks may include at least in part a resorbable material or bioresorbable material which can further be impregnated with a bone growth material so that as the resorbable material or bioresorbable material is resorbed by the body of the patient, the bone growth material is released, thus acting as a time release mechanism. The bioresorbable material may be, for example, at least in part other than bone. The plating system of the present invention may be used in combination with a spinal fixation implant such as any object, regardless of material, that can be inserted into any portion of the spine, such as but not limited to interbody spinal implants, interbody spinal fusion implants, structural bone grafts, mesh, cages, spacers, staples, bone screws, plates, rods, tethers of synthetic cords or wires, or other spinal fixation hardware. The interbody spinal fusion implant may be comprised at least in part of bone. The interbody spinal fusion implant may be, for example only, an allograft interbody bone graft implant, or an artificial implant. At least one of the vertebral body engaging anchors, connecting plate, and fasteners may be, if so desired, electrified for purposes of stimulating bone growth and contributing to bone fusion.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for stabilizing at least two adjacent vertebral bodies in the cervical human spine, comprising:
providing a plate system adapted to be applied to the anterior aspects of an anterior human cervical spine for contacting the anterior aspects of at least two cervical vertebral bodies to be fused together, the plate system having at least a first vertebral body engaging anchor adapted to be attached to one of the adjacent vertebral bodies to be fused and at least a second vertebral body engaging anchor adapted to be attached to another one of the adjacent vertebral bodies to be fused, a connecting plate configured to connect the first and second vertebral body engaging anchors, and at least two fasteners, each of the fasteners adapted to couple together the connecting plate and one of the first and second vertebral body engaging anchors;
inserting at least two bone screws through the first vertebral body engaging anchor of the plate system and into one of the vertebral bodies adjacent the disc space to be fused;
inserting at least two bone screws through the second vertebral body engaging anchor and into the other of the vertebral bodies adjacent the disc space to be fused;
connecting the first and second vertebral body engaging anchors with the connecting plate, the connecting plate overlapping at least a portion of each of said first and second vertebral body engaging anchors;
fastening together said connecting plate and the first and second vertebral body engaging anchors with at least two fasteners, each of the fasteners being tightened to and being in a fixed position relative to only one of the connecting plate and the first and second vertebral body engaging anchors without each fastener protruding above the connecting plate; and
with the fasteners being in the fixed position relative to only one of the connecting plate and the first and second vertebral body engaging anchors without the fasteners protruding above the connecting plate, permitting movement of the first and second vertebral body engaging anchors attached to the adjacent vertebral bodies relative to the connecting plate and relative to one another.

2. The method of claim 1, wherein the permitting movement of the first and second vertebral body engaging anchors includes permitting movement of the first and second vertebral body engaging anchors in only a single direction toward one another.

3. The method of claim 1, wherein the permitting movement of the first and second vertebral body engaging anchors includes allowing but not causing the movement of the adjacent vertebral bodies by movement of the first and second vertebral body engaging anchors relative to the connecting plate.

4. The method of claim 3, wherein the permitting movement of the first and second vertebral body engaging anchors includes the first and second vertebral body engaging anchors being free to move toward one another.

5. The method of claim 1, wherein the permitting movement of the first and second vertebral body engaging anchors includes allowing movement of the first and second vertebral body engaging anchors of the plate in response to movement of the adjacent vertebral bodies.

6. The method of claim 1, wherein the permitting movement of the first and second vertebral body engaging anchors includes limiting the movement of the first and second vertebral body engaging anchors relative to one another to sequential increments along the longitudinal axis of the connecting plate.

7. The method of claim 1, wherein the permitting movement of the first and second vertebral body engaging anchors includes causing movement of the adjacent vertebral bodies by moving the first and second vertebral body engaging anchors relative to one another and relative to the connecting plate.

8. The method of claim 7, wherein the causing movement of the adjacent vertebral bodies includes generating a compressive load across the disc space between the adjacent vertebral bodies.

9. The method of claim 8, wherein the permitting movement of the first and second vertebral body engaging anchors includes the first and second vertebral body engaging anchors being free to move toward one another.

10. The method of claim 7, wherein the causing movement of the adjacent vertebral bodies includes storing a compressive load across the disc space between the adjacent vertebral bodies.

11. The method of claim 1, further comprising applying a compressive load to the adjacent vertebral bodies.

12. The method of claim 1, further comprising aligning the first vertebral body engaging anchor with the second vertebral body engaging anchor prior to the connecting the first and second vertebral body engaging anchors with the connecting plate.

13. The method of claim 1, wherein the permitting movement of the first and second vertebral body engaging anchors includes moving the first and second vertebral body engaging anchors from a first position to a second position.

14. The method of claim 1, wherein the tightening of the first and second fasteners to the first and second vertebral body engaging anchors includes resisting movement of the first and second vertebral body engaging anchors relative to the connecting plate in at least one direction.

15. The method of claim 14, wherein the tightening of the first and second fasteners to the first and second vertebral body engaging anchors includes resisting movement of the first and second vertebral body engaging anchors relative to one another.

16. The method of claim 1, wherein the tightening of the first and second fasteners to the first and second vertebral body engaging anchors includes limiting the movement of the first and second vertebral body engaging anchors relative to one another to one direction along a longitudinal axis of the connecting plate.

17. The method of claim 1, wherein the tightening of the first and second fasteners to the first and second vertebral body engaging anchors includes limiting the movement of the first and second vertebral body engaging anchors relative to one another to sequential increments along a longitudinal axis of the connecting plate.

18. The method of claim 1, wherein the providing a plate system includes providing a plate system having at least a third vertebral body engaging anchor.

19. The method of claim 1, further comprising locking the at least two of the bone screws with at least a portion of the connecting plate.

20. The method of claim 1, further comprising combining the plate system with an interbody spinal fusion implant.

21. The method of claim 20, wherein the implant comprises at least in part bone.

22. The method of claim 20, wherein the implant is an allograft interbody bone graft implant.

23. The method of claim 1, further comprising combining the plate system with a fusion promoting substance.

24. The method of claim 23, wherein the fusion promoting substance is at least in part other than bone.

25. The method of claim 23, wherein the fusion promoting substance is at least in part bone.

26. The method of claim 23, wherein the fusion promoting substance is hydroxyapatite.

27. The method of claim 23, wherein the fusion promoting substance comprises bone morphogenetic protein.

28. The method of claim 23, wherein the fusion promoting substance comprises genes coding for the production of bone.

29. The method of claim 1, wherein at least a portion of one of the vertebral body engaging anchors, the connecting plate, the fastener, and the bone screws is a bioresorbable material.

30. The method of claim 29, wherein the bioresorbable material is at least in part bone.

31. The method of claim 1, further comprising combining at least one of the vertebral body engaging anchors, the connecting plate, the fasteners, and the bone screws with a substance for inhibiting scar formation.

32. The method of claim 1, further comprising combining at least one of the vertebral body engaging anchors, the connecting plate, the fasteners, and the bone screws with an antimicrobial material.

33. The method of claim 1, further comprising treating at least one of the vertebral body engaging anchors, the connecting plate, the fasteners, and the bone screws with an antimicrobial material.

34. The method of claim 1, further comprising electrifying at least one of the vertebral body engaging anchors, the connecting plate, the fastener, and the bone screws with an antimicrobial material for purposes of stimulating bone growth and contributing to bone fusion.

35. The method of claim 1, wherein the providing the plate system includes providing first and second vertebral body engaging anchors that are each a unitary structure.

36. The method of claim 1, further comprising using an alignment instrument to align at least the first and second vertebral body engaging anchors relative to one another and to position the first and second vertebral body engaging anchors against the anterior aspects of the adjacent vertebral bodies of the human cervical spine.

* * * * *